(12) United States Patent
Sambusseti

(10) Patent No.: US 9,393,098 B2
(45) Date of Patent: Jul. 19, 2016

(54) ABSORBABLE CAP FOR BLADDER ENLARGEMENT IN PATIENTS WITH LOW COMPLIANCE OR FOR THE REPLACEMENT OF A VAST PORTION OF BLADDER FOLLOWING BILHARZIA

(71) Applicant: Antonio Sambusseti, Cremona (IT)

(72) Inventor: Antonio Sambusseti, Cremona (IT)

(*) Notice: Subject to any disclaimer, the term of this patent is extended or adjusted under 35 U.S.C. 154(b) by 0 days.

(21) Appl. No.: 14/382,571

(22) PCT Filed: Mar. 6, 2013

(86) PCT No.: PCT/EP2013/054538
§ 371 (c)(1),
(2) Date: Sep. 3, 2014

(87) PCT Pub. No.: WO2013/135543
PCT Pub. Date: Sep. 19, 2013

(65) Prior Publication Data
US 2015/0045907 A1    Feb. 12, 2015

(30) Foreign Application Priority Data

Mar. 12, 2012 (IT) .............................. MI2012A0380

(51) Int. Cl.
*A61F 2/04* (2013.01)
*A61M 29/00* (2006.01)
*A61L 31/06* (2006.01)
*A61L 31/14* (2006.01)
*A61F 2/00* (2006.01)

(52) U.S. Cl.
CPC ................. *A61F 2/042* (2013.01); *A61L 31/06* (2013.01); *A61L 31/14* (2013.01); *A61L 31/148* (2013.01); *A61M 29/00* (2013.01); *A61F 2/0063* (2013.01); *A61L 2430/22* (2013.01)

(58) Field of Classification Search
CPC .......... A61F 2/04; A61F 2/042; A61F 2/0063
See application file for complete search history.

(56) References Cited

U.S. PATENT DOCUMENTS

| 6,966,918 B1* | 11/2005 | Schuldt-Hempe .... A61F 2/0063 606/151 |
| 2002/0055786 A1 | 5/2002 | Atala |
| 2005/0113938 A1 | 5/2005 | Jamiolkowski et al. |
| 2005/0283246 A1* | 12/2005 | Cauthen, III ....... A61B 17/0057 623/17.16 |

(Continued)

FOREIGN PATENT DOCUMENTS

| WO | 2007/095193 | 8/2007 |
| WO | 2011/018300 | 2/2011 |

(Continued)

OTHER PUBLICATIONS

International Search Report dated Mar. 28, 2013, corresponding to PCT/EP2013/054538.

*Primary Examiner* — Thomas J Sweet
*Assistant Examiner* — Daniel Bissing
(74) *Attorney, Agent, or Firm* — Young & Thompson

(57) ABSTRACT

A description is given of a domed cap (100) for the enlargement of an atrophied bladder (200), in biocompatible and absorbable material including a textile (1) made with yarns or with monofilaments deriving from PGA fibers, characterized in that the textile (1) is supported by a star-shaped frame with domed profile, formed by a plurality of radial strips (3) manufactured by injection of a PGA/PLA copolymer, the cap (100) being suitable for growing thereon autologous fibrous capsule cells, generated by the process of tissue reconstruction, after its insertion inside the patient.

20 Claims, 3 Drawing Sheets

(56) References Cited

U.S. PATENT DOCUMENTS

2011/0319977 A1* 12/2011 Pandelidis ............ A61L 27/047
 623/1.15
2012/0172998 A1* 7/2012 Oishi ........................ A61F 2/28
 623/23.61

FOREIGN PATENT DOCUMENTS

| WO | WO 2011018300 A1 * | 2/2011 | ............ A61F 2/0063 |
| WO | 2011/064110 | 6/2011 | |
| WO | WO 2011064110 A1 * | 6/2011 | .............. A61F 2/042 |

* cited by examiner

ABSORBABLE CAP FOR BLADDER ENLARGEMENT IN PATIENTS WITH LOW COMPLIANCE OR FOR THE REPLACEMENT OF A VAST PORTION OF BLADDER FOLLOWING BILHARZIA

BACKGROUND OF THE INVENTION

1. Field of the Invention

The present invention relates to an improved absorbable cap for bladder enlargement in patients with low compliance (low filling capacity) in the treatment and therapy of atrophied bladders, but also for the replacement of a vast portion of bladder following bilharzia.

2. Description of the Related Art

Patients with low compliance generally have an atrophied bladder whose volume is about 150-200 cc, much smaller than the volume of a healthy bladder which is normally around 400 cc. This entails, as is intuitive, serious problems for the patient.

Moreover low compliance is associated in general with the disorder of incontinence and of urine leakage when coughing or during effort.

In order to overcome these disadvantages surgical treatment is adopted which lies in the implanting, on the atrophied bladder, of a prosthesis of hemispherical or cap shape and internally hollow in order to increase the overall volume of the expanded bladder.

This prosthesis is generally made with the intestine tissue of the actual patient in order to have high compatibility, reduced rejection and reduced formation of the fibrous capsule.

However the tissue of the intestine does not always have the same mechanical properties as the tissue of the bladder, such as for example elasticity, nor the ability to assume stably a substantially hemisphere shape which is necessary in order to supply a constant volume of expansion of the bladder and maintain it as such.

To this end the Applicant has developed an absorbable domed cap, internally hollow, of textile in PGA and reinforced with strips of the same textile, which allows the technical problem described above to be solved. See patent application MI2011A000386.

However, following further tests, the Applicant has found that this cap very often tends to collapse during the growth of the neotissue after the implant, very probably due to the weight of the growing neotissue after the implant: this causes a smaller increase in volume compared to that supplied by a non-subsiding cap which maintains its round domed profile also under the weight of the growing neotissue. Moreover this known cap tends to create adherences inside the abdomen, in the implant point. See the test reproduced below.

WO2011/064110 describes a planar patch of textile in PGA with reinforcement strips made with the same textile in PGA, to be used for the reconstruction of a portion of bladder wall following a partial cystectomy.

This patch however, being made throughout with fibres of PGA homopolymer, has an absorption time of the order of 30 days, similar to the time of growth of bladder neotissue: this entails a decline in the mechanical properties during this period of absorption which consequently leads to the collapse of said patch inside the bladder under the weight of the new growing tissue, given the decreased rigidity and load-bearing capacity in said space of time, similar to what is described above.

US 2005/0113938 describes a biocompatible implant for the reconstruction of tissues, different from the bladder tissue, formed by a foam made up, among others, of PGA/PLA which is reinforced with textile or porous elements, formed, among others, by fibres of PGA/PLA.

This implant is however poorly suitable for a bladder enlargement in view of the high porosity, both of the foam and of the reinforcement elements, which, although on the one hand ensures the populating of the implant by the growing neotissue, on the other hand determines an undesirable leakage of urine from the bladder during the growth of the autologous neotissue.

BRIEF SUMMARY OF THE INVENTION

Moreover both the solutions of the aforementioned prior art have little possibility of adapting during surgery to the specific curved shape of the portion of bladder removed. The object of the present invention is to eliminate, at least in part, the disadvantages of the prior art, by providing a domed device specifically for bladder enlargement in patients with low compliance, which is elastic/flexible such as to ensure the correct deformation of the device during the physiological functioning of the bladder whereon it is attached, yet also with improved rigidity, and constant during the time of growth of the neotissue, such as not to collapse, at least in part, in said space of time so as to allow, after implant, a growth of the neotissue with a round shape, so as to conserve in time the volume restored by said device.

Another object of the present invention is to provide such a device which is also with zero rejection, provided with high compatibility and possibly also absorbability with lack of adherences to the fibrous capsule, which is reliable without exhibiting possible leaks and/or releases of liquid and is resistant to urine and impermeable thereto.

A further object is moreover that of supplying such a cap device which also exhibits a high possibility of conforming during the operation to the specific curved shape of the portion of bladder removed.

These and other objects are achieved by an improved cap device in biocompatible and absorbable textile according to the invention.

Advantageous embodiments of the invention are disclosed by the dependent claims.

The device according to the invention for the enlargement of the atrophied bladder is made up of a domed cap, with round profile, formed essentially by two elements coupled one to the other: a textile in biocompatible and absorbable material suitable for ensuring the absence of fibrous capsule around it once the cap has been implanted, avoiding a subsequent removal procedure; a self-supporting frame with domed profile for the support of this textile made in a rigid yet flexible material also biocompatible and absorbable.

The internal and external surfaces of said cap are without sowing of cultured cells and in this condition the cap is implanted in the patient, in the absence of any previous covering by cultured tissue cells and any surface treatment suitable for encouraging the grafting of the growing tissues.

In practice the aforesaid cap, ready for use without any previous cell covering, has been found to be suitable for acting as scaffold after insertion inside the patient, making grow on it only autologous fibrous capsule cells, generated by the process of tissue reconstruction of the patient, which only takes place after its insertion.

The textile of the cap is made by using an ultra-lightweight monofilament or yarn, deriving from fibres of PGA (polyglycolide or polyglycolic acid), preferably homopolymer: said PGA is a highly biocompatible and absorbable polymer, as well as resistant to urine.

The textile of the cap of the present invention can be made by weaving, in various ways, a monofilament or yarn in PGA, creating a knit textile, a woven textile or a nonwoven textile.

A knit textile is preferred, more preferably warp knit, in that provided with a more wrinkled surface compared to other manufactured types and able to take on a mesh configuration whose meshes (holes) are very small.

The use of a textile rather than a foam is advantageous in that it has porosity sufficient for facilitating the growth of the neotissue without however being such as to make the urine leak from the device during the growth of the neotissue.

Said textile is moreover preferably texturised. It has in fact been found that texturisation, in addition to making the textile more wrinkled on the surface, also confers a greater rigidity and impermeability to urine compared to a non-texturised textile. In fact it is believed that the texturisation goes to cover the micro holes which exist between the meshes of the textile.

The texturisation of the textile can be performed in various ways: by means of the use of monofilament with wrinkled surface obtained according to the methods known in the art, or by means of a heat-setting treatment of the textile in order to obtain raised parts in the fibres conferring greater volume to the filament. This latter method of texturisation is preferred.

The textile, before being coupled to the frame, has a generally circular plan profile and of such a size as to be able to obtain a cap with diameter of approximately 8-10 cm. However these dimensions are not binding for the purpose of the present invention, and the textile to be coupled to the frame can also be obtained from a textile of larger size, for example 10 cm×15 cm.

The thickness of the aforesaid textile is not binding for the purpose of the present invention: it is sufficient for ensuring the elasticity and the flexibility necessary for the movements (dilations) of expansion and collapsing of the bladder due to the filling and emptying of the same yet at the same time is fairly small. Generally the thickness of the textile can vary between 0.1 mm and 2 cm. In a preferred embodiment said thickness is approximately 0.3-0.6 mm, more preferably approximately 0.4-0.53 mm, even more preferably 0.45 mm.

The aforementioned frame is formed by a plurality of curved and heat-formed radial strips, or arms, substantially rigid but elastic and provided with a slight curvature which allows the frame to take on a domed configuration.

Moreover said strips extend from the central point on the top of said frame radially outwards like rays or arms of a star.

Said frame, called as BIOSTAR, was produced on behalf of the Applicant by Mr. Christian Choux.

The frame is obtained by means of injection of a copolymer of glycolic acid and lactic acid, indicated as PGA/PLA (poly(lactic-co-glycolic)acid), whose domed shape with slight curvature of the radial strips is imparted with heat by means of heat forming.

Heat forming is a technique of hot moulding of plastic materials from sheets or films, under pressure or vacuum, for example by preheating the sheet or the film of plastic polymer and then laying on the mould this preheated material. Or by pushing the plastic film on the mould thanks to a high pressure exerted from the outside by the air, which also facilitates the cooling thereof. Or by using a mould and counter-mould system actuated mechanically with the aid of hydraulic presses.

This technique enables homogeneous and non-porous elements to be obtained, without surface holes and/or holes inside the bulk of the element, and cannot be used for obtaining fibres of PGA/PLA which are instead formed by using specific methods for the obtaining of fibres such as meltspun, electrospun and the like.

Since lactic acid is a chiral molecule, there are different types of polymer, PDLA, PLLA, PDLLA, where D and L represent the two stereoisomers. PLLA has a crystallinity of 37%, a temperature of glass transition between 50 and 80° C., and a melting point of 173-178° C., while the polymer deriving from the polymerisation of a racemic mixture, PDLLA, is amorphous.

The term poly(lactic) acid is intended here to identify all the various types of PLA polymer indicated above.

Said frame constitutes the support structure of the aforementioned textile, allowing the latter to take on a domed configuration suitable for defining and providing a certain volume, generally around 200 cc.

Once this frame has been obtained, which is found to be flexible and elastic, it is attached to the textile in PGA, on the surface of the textile turned towards the exterior of the bladder, stitching it with suture stitches of absorbable thread, for example with a monofilament in polydioxanone (PDO) with slow absorption such as absorbable MONOTIME®.

Generally the thickness of the frame and of the relative strips (arms) can vary between 0.1 and 10 mm, preferably between 0.5 and 2 mm. In a preferred embodiment said thickness is approximately 1 mm.

Since the textile in PGA and the frame in PGA/PLA are absorbed in approximately 1 month and the time of reforming of the polyprotein capsule which will act as enlargement of the new bladder is substantially the same, it is clear that the implanted cap does not subsequently have to be removed as it is absorbable substantially with the same rate of growth of the new tissue.

More particularly, the heat-formed frame in PGA/PLA, which exhibits a complete absorption after 5-6 months, maintains its rigidity and mechanical properties constant in the first month of absorption and growth of the bladder neotissue so as to ensure that the device does not give way inside the bladder under the weight of the growing bladder neotissue in this space of time.

Moreover during the subsequent 150 days (approximately) after absorption of the textile in PGA, the presence of residual PLA/PGA of the frame during absorption provides an incentive for improvement of the neotissue formed after the first 30 days, since it helps the bladder neotissue to reach in a total of 180 days an optimal profile, consistency, shape and dimension.

The support structure of the frame therefore has the purpose of supporting the textile which forms the dome for the 30 days necessary for its absorption so as not to make it collapse and to give to the neotissue a shape and profile identical to the original ones of the portion removed, i.e. curved.

BRIEF DESCRIPTION OF THE DRAWINGS

Further features of the invention will be made clearer by the following detailed description, referred to one of its embodiments purely by way of a non-limiting example illustrated in the accompanying drawings, in which:

Referring to FIGS. 3-4, a cap is described, denoted overall by reference numeral 100, suitable for use as implant for bladder enlargement in patients with low compliance.

DETAILED DESCRIPTION OF THE PREFERRED EMBODIMENTS

Said cap is formed by a flat textile 1, with circular profile, which is coupled to a frame formed by a plurality of radial reinforcement strips 3, slightly curved, each one forming a portion of arc, more particularly a semi arc, which departs from the top of the frame downwards, similarly to the frame of an umbrella.

This is advantageous in that the support action exerted by the frame is identical in each radial curved strip starting from the top of the dome, allowing uniform growth of the textile in space.

This frame therefore acts as support structure for the textile 1, enabling it to take on, evenly in space, a dome shape which is maintained as such also under the weight of the tissue growth, thus obtaining a self-supporting cap.

Figure 4:
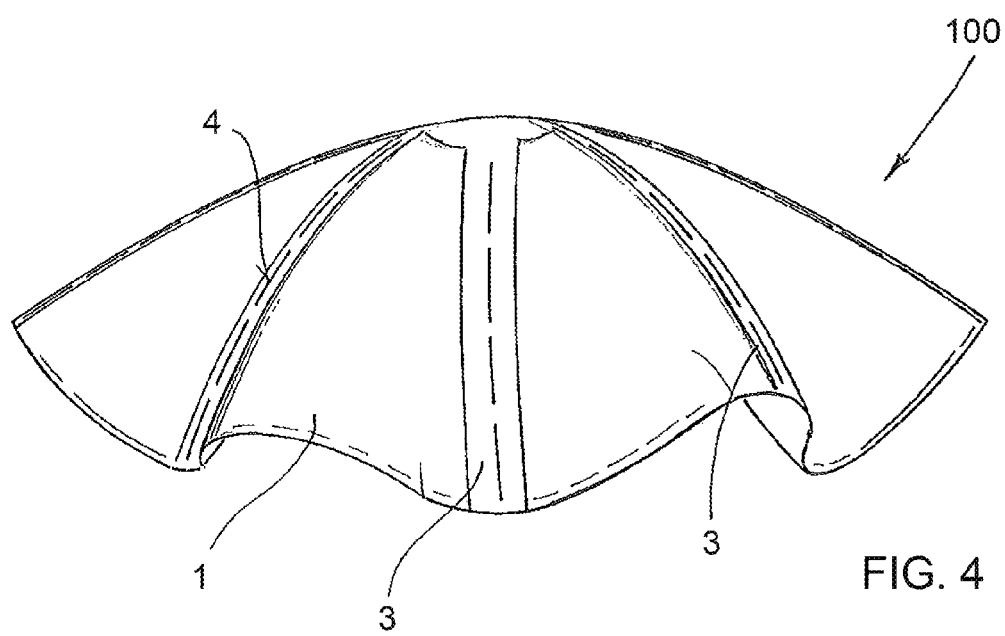
FIG. 4 is a side view of the cap before the implanting in the patient.

The frame and the reinforcement strips 3 which are placed on the upper surface 2 of the textile 1 are attached thereto by means of absorbable sutures 4 (FIG. 4), defining the same number of sectors on the upper surface 2 of the textile 1. Thanks to these sutures 4 it is possible to avoid the use of adhesive materials which could produce undesirable reactions.

In this embodiment the total thickness of the cap 100 inclusive of frame and textile 1 is approximately 1.45 mm even if this is not binding for the purpose of the present invention.

The PGA/PLA copolymer of the frame can be formed, for example, by 30% of PGA and by 70% of PLA.

Particularly preferred as PLA/PGA copolymer (poly (lactic-co-glycolic) acid) is the poly(L-lactic-co-glycolic) copolymer (PLLA/PGA) wherein the L-lactic acid is 82-88% in moles while the glycolic acid is 18-12% in moles. This copolymer is known commercially by the name Resomer® LG 855S.

As mentioned the textile 1 is preferably warp knitted. In this case its weave is such that the interstitial space is less than 200 microns, preferably around 160 microns, corresponding to an average area of the holes equal to approximately 0.02 mm². This guarantees impermeability to urine, avoiding leaks.

Moreover said textile 1 is made with yarns having dimensions of approximately 50-200 deniers, monofilament or multifilament, preferably multifilament.

The warp knitting manufacture does not allow a woven or a nonwoven or a felt-like material to be obtained.

This process of warp knitting is performed on a machine for warp knitting with a density of 30 needles/inch, where the yarns are parallel warps and knitted at the same time, preferably with a pattern of manufacture of the type

| Wales Per Inch (WPI) | 29-30 |
|---|---|
| Courses Per Inch (CPI) | 62-68 |

With this manufacturing pattern and with the preferred yarn indicated above a textile 100 is obtained, having the following features:

| Average area (mm²) | 0.020 |
|---|---|
| Effective diameter (microns) | 140-180 |
| Porosity | 70-80% |
| Surface density, mg/cm² | 16-18 |

The upper 2 and lower 2' surfaces (FIG. 2) of the textile 1 are presented as very wrinkled because, preferably, they are subjected to texturisation, in addition to the warp knit manufacture, in order to increase further the non-adherence to the fibrous capsule.

Upper surface refers to the surface of the textile 1 turned towards the exterior of the bladder and intended to come into contact with the internal tissues of the patient, while lower surface of the textile 1 refers to that turned towards the interior of said bladder which is intended to come into contact with the urine.

The textile 2 is preferably texturised and made with a 75 deniers/30 filaments (parallel one to the other) yarn, where 75 deniers is the dimension of the yarn corresponding to 75 g/10000 yards of yarn (10000 yards~9000 meters) and 30 is the number of smaller threads which form each yarn.

The Applicant has surprisingly found that the cap 100 made with a textile 1 in PGA as described above, more particularly texturised, in combination with a frame in PGA/PLA, exhibits a good mechanical consistency and sufficient rigidity and elasticity, also in the presence of urine, so that it is able to guarantee a correct deformation of the bladder during the emptying or the filling of the same, exhibiting at the same time a good tightness against leaks of urine.

Moreover the aforesaid textile, and also the non-porous frame, are found to be neutral when in contact with growing bladder neotissue: this entails a rapid population of the device implanted by the cells of the growing surrounding tissue. At the same time the adhesion was found to be reduced due to the reduced interaction among the polymers which make up the textile/frame and the biological molecules, thus ensuring a non-fusion with the internal tissues of the patient.

Figure 1:
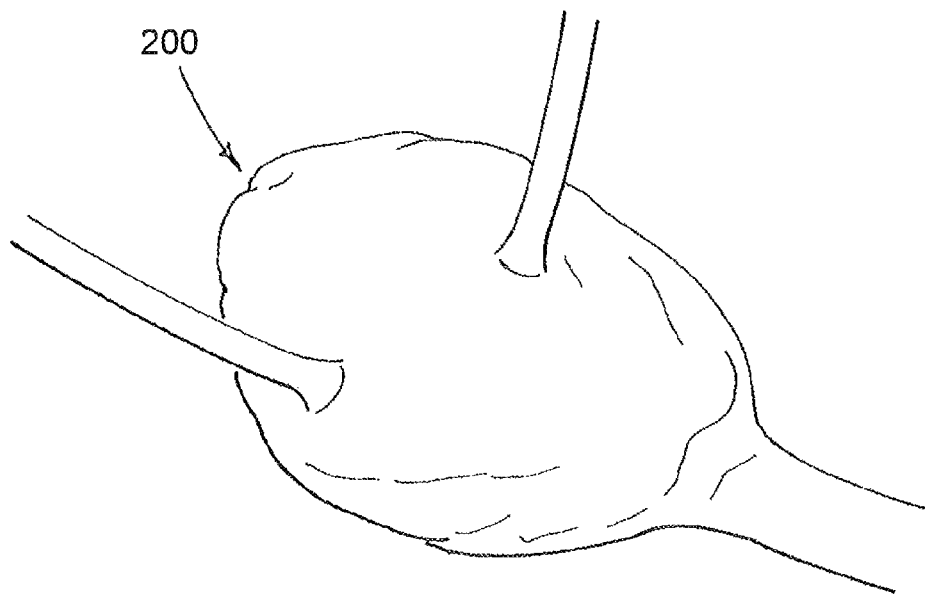
FIG. 1 is a perspective view of a bladder with low compliance with relative ureters and urethra.
Figure 2:
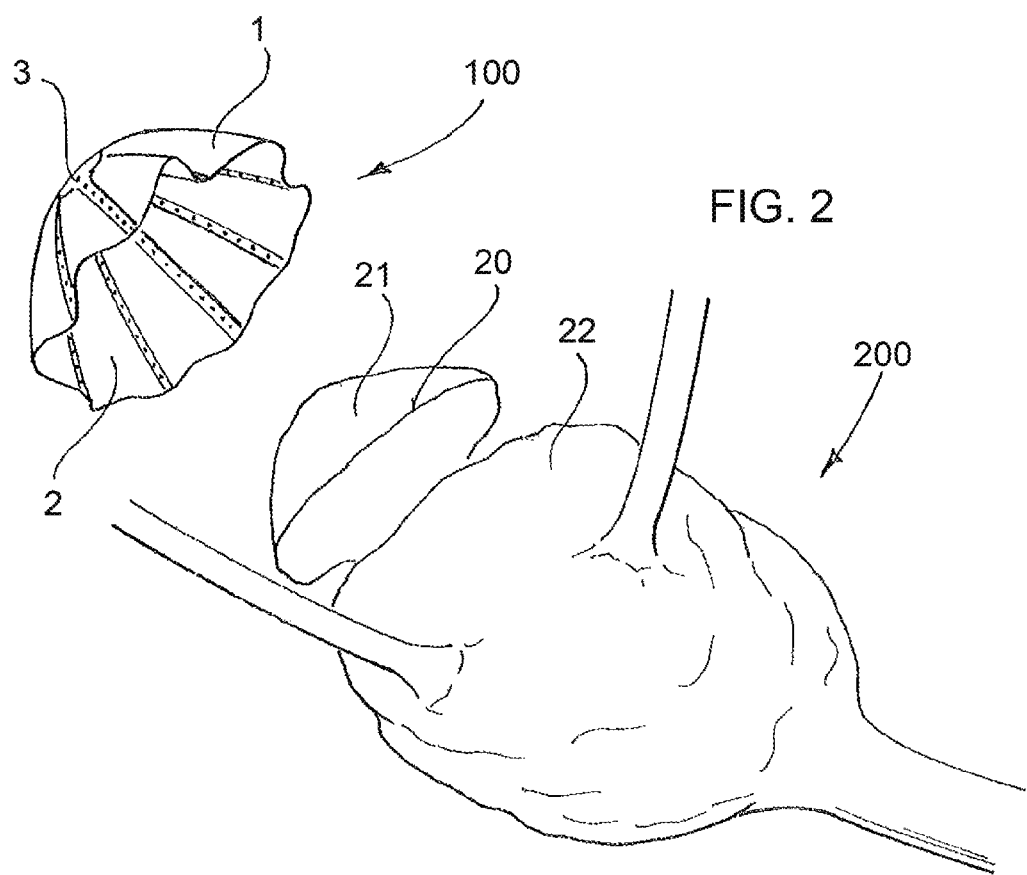
FIG. 2 is a perspective view of the bladder of FIG. 1 wherein the upper part has been cut in order to be replaced by a cap formed by the device of the invention.
Figure 3:
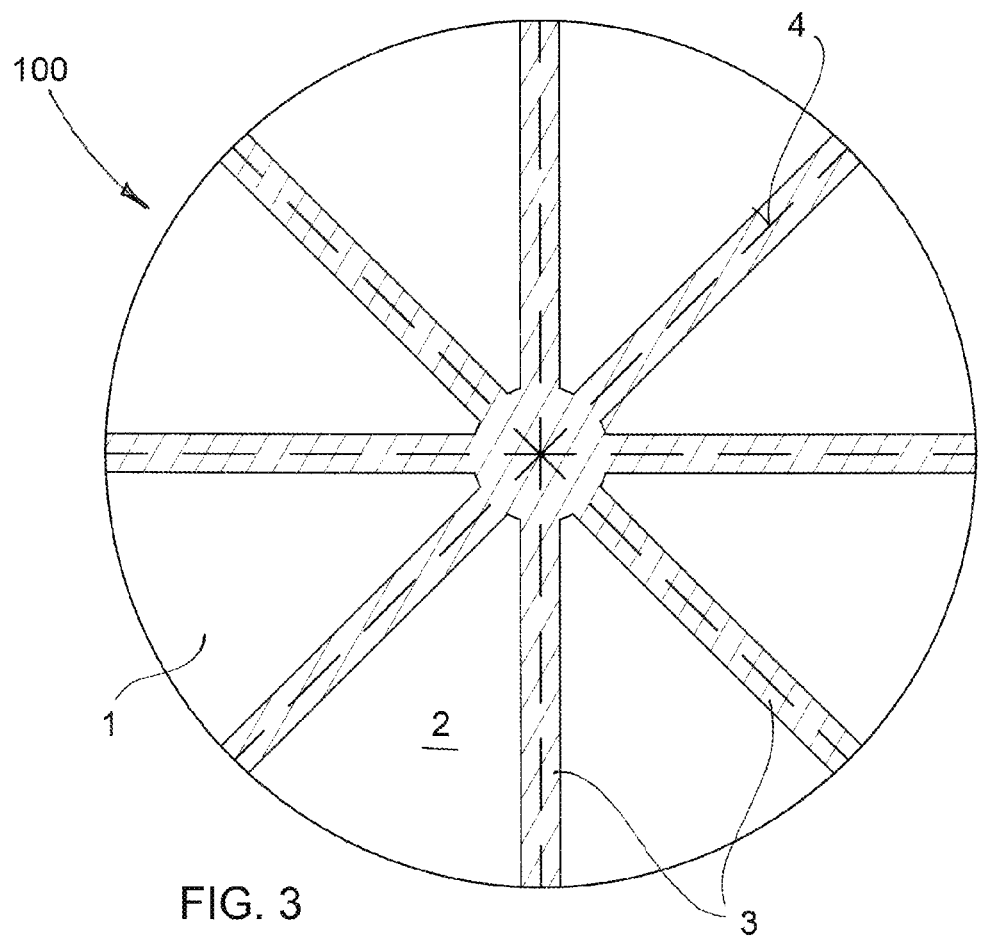
FIG. 3 is a plan view from above of the cap of FIG. 2.

Referring to FIGS. 1-2, during the operation of implanting the cap is sutured around the edge of the incision made on the bladder or of the half bladder 22 not removed. In fact the atrophied bladder 200 can be first cut into two parts, the upper part 21 whereof (FIG. 2) is removed while around the perimeter of the lower part 22 not removed the edge of the textile 1 of the cap 100 is sutured.

Figures 5A, 5B:
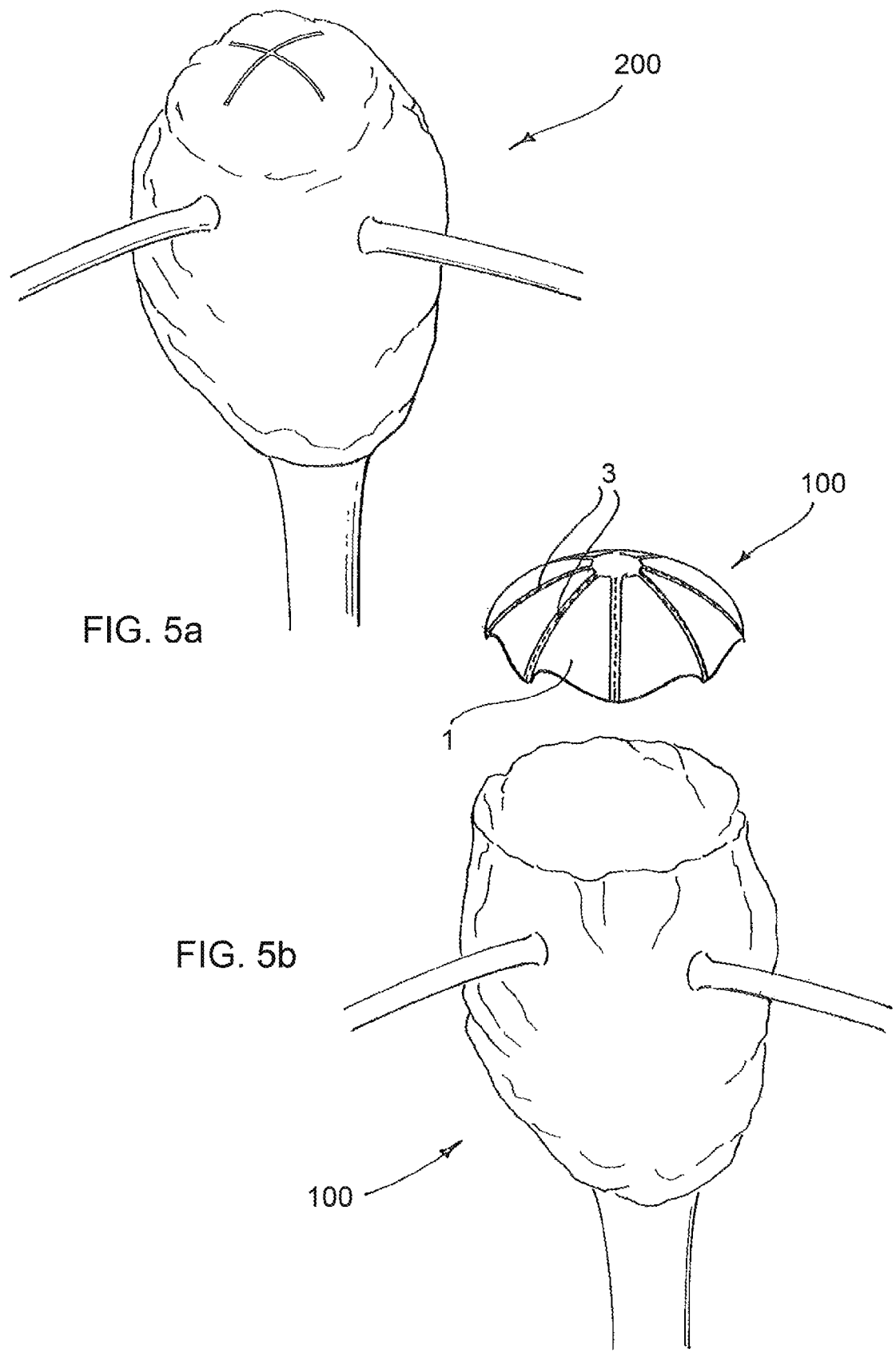
FIGS. 5a)-b) are perspective views of the atrophied bladder in the phases of cutting and enlargement by insertion of the cap.

Alternatively the atrophied bladder 200, comprising ureters and urethra, is only incised with a cross cut, opened and subsequently sutured to the cap 100, around the edge of the opening created by the cut (FIGS. 5a), 5b)).

In the case of replacement of a vast portion of bladder following bilharzia, the cap 100 is sutured around the perimeter of the lower part 22, after having removed the portion of bladder 21 (FIG. 2) affected by the aforementioned disease.

After the implanting, over this cap 100 the neotissue will then form that comes from the natural growth of the polyprotein capsule around the implant, without having to use cultured cells.

Alternatively it is possible to adopt another surgical technique of dome implanting, both in the case of low compliance and in the case of replacement due to bilharzia, performing a removal of the portion of bladder placed above the bladder plate or trigone, from approximately 1 cm above the trigone upwards, without however touching urethra and ureters: the tissue above this height is removed and the dome positioned and sutured to the edges of the tissue remaining all around and above the bladder trigone.

For the suture a suture thread in absorbable material (PGA), with dimensions of approximately 4/0, is preferably used. The reasons for this choice lie in the need for the cap and sutures to be absorbed in the same timespan. The suture thread is then inserted in a round ¾ curved cylindrical needle, including the "Bassini" ones.

Other suture threads in bioabsorbable polymers in any case exist which could be conveniently adapted to the case in question and to the needs at the discretion of the surgeon.

The holes of passage of the suture stitches in the bladder do not constitute a risk of liquid leaks, in that the tissue is reconstructed in a few hours. To avoid leaks of urine (liquid), the holes of the suture stitches are sealed and closed with a cc (a drop) of surgical glue, such as for example Glubran 2™, normally available commercially.

The same can be repeated and performed for the holes of the suture stitches which connect the frame to the textile.

One of the advantages of the cap of the present invention is that it does not have any risk of adherence of the fibrous capsule and that it does not require the removal from the organ wherein it has been implanted in that it is completely absorbable during the regeneration of the tissue. The time of complete absorption may vary from 1 month to approximately 2 months according to the metabolism of the patient and the features of the textile 1 for cap indicated previously.

The cap 100 is prepared in, a controlled environment that is to say with controlled contamination, in a white room. Once processing has finished, the cap 100 is enclosed by a sheet of Tyvek to avoid contaminations, and sent to a cycle of sterilisation with gamma rays. At this point the cap 100 is ready to be used in an operation.

The present cap 100 has a series of advantages with respect to the known devices used for the same purpose: with respect to the cap described in the patent application MI2011A000386 and WO2011/064110, the present cap is not subject to subsiding, in addition to not having adherences inside the abdomen, in the point of implant. This encourages tissue growth with a dome shape.

Moreover the present cap 100 is both collapsible (elastic) during emptying and harmonic thanks to the star structure of the frame in copolymer of PGA/PLA: thanks to it the textile 1 of the cap 100 can follow the normal and physiological expansion and contraction of the bladder during the period of implant without however giving way under the weight of the growing neotissue.

Ultimately the improvement brought to the present cap by the use of a frame in copolymer of PGA/PLA lies in its harmonicity (i.e. elasticity similar to the harmonic steels used in springs), flexibility and rigidity which allow the present cap to follow both the physiological movement of expansion and contraction of the bladder and to maintain the cap fairly rigid so as not to give way and create adherences.

Another advantage lies in the fact that, unlike other devices, said cap is not to be removed, in that completely absorbable, and that said cap can be shaped in situ following the anatomical profile of the point of implant, thanks to the harmonicity of the support frame.

In fact, given its light harmonicity and malleability, the frame can be slightly modified in the shape and in the curvature, by means of manual manipulation by the surgeon, in the phase of implant on the basis of the needs of each single case or of each single point of implant again in the bladder area.

Moreover with respect to other devices in PLA alone, the present cap has a better quality of tissue reconstruction, in that there are no hypertrophic residues which are instead present in the devices in PLA, even if these residues in the long term tend to disappear.

In fact even if the time of absorption of the PLA is greater than the PGA (indeed internally after 60 days some particles of PLA are found which require at least 30 days more for total absorption) the quality of tissue reconstruction is excellent, similar to other hemisphere shaped devices.

Additionally, with respect to other known implants, the present cap does not need to be covered with cultured cells in order to be implanted, since it has been found that, after insertion inside the patient, it is covered by only autologous fibrous capsule cells, generated by the process of tissue reconstruction of the patient, without needing any surface treatment in order to encourage the grafting of the growing tissues, therefore acting as a scaffold.

In practice the present cap enables the avoiding of a series of long and complex phases necessary with other known devices, such as the initial phase of isolation of the cells to be cultivated by means of biopsy, phase of growing of the number of cells isolated and phase of population, as well as a phase of pretreatment of the surface of the cap so that it can be populated by the cells.

In fact the cap of the present invention advantageously possesses the following combination of good properties:
sufficient rigidity, constant during the time of growth of the bladder neotissue, such as to allow the bladder to maintain its shape until absorption of the cap and, at the same time, not to collapse under the weight of the growing tissues, resulting in a self-supporting device during the entire aforesaid space of time;
sufficient elasticity and flexibility such as to ensure the correct deformation of the device during the physiological functioning of the bladder whereon it is attached;
chemical resistance and impermeability to urine;
capability to be covered by the neotissue, even if not porous;
non-collapsibility;
non-adherence to the fibrous capsule;
greater rigidity compared to that of devices intended for the same use yet having reinforcements made in a textile, for example in PGA/PLA;
greater possibility of shaping during the operation thanks to heat-formed reinforcements in harmonic PGA/PLA which can be slightly curved manually by the surgeon if necessary.

Tests performed by the Applicant using similar devices in a textile with textile reinforcements, made completely of PGA, such as those described in WO2011/064110, have shown that this latter polymer, widely used with success in the medical sector, cannot be used advantageously for bladder enlargement.

More particularly preclinical studies have been performed in vivo on a pig bladder implanted with a round patch (7 cm in diameter) in monofilament PGA, texturised, having a denier count similar to that of the present textile in PGA between 50 and 200 deniers, with reinforcement strips taken from the same textile in PGA, in order to evaluate the behaviour of the device in place of a portion of bladder in the time of absorption (1 month) by means of the analysis of the scarring, of the integration of the patch in the tissues, of the functioning of the kidneys, of the lack of local systemic effects. The animal was kept under control by means of laboratory analyses and ultrasound scan starting from the day of the operation up to the end of the first month (time of absorption of the PGA).

After 14 days it was observed via the ultrasound scan that the device had attached to the walls of the bladder and that the site of the implant exhibited a remodelling with thickening of the bladder wall in its proximity.

The examination at two months from the implant demonstrated adherences of the intestine and of the uterus to the zone of the bladder whereon the patch was implanted, and the presence of zones of dark colour in the scar of the implant zone, indication of the remodelling of the zone.

Moreover the histological examination of this implant zone showed that the scar was formed by mature granulation tissue and incorporated the remaining patch.

These phenomena indicate that the vast portion of bladder removed was not replaced by a new wall of cell tissue of the same dimensions and that the device must have collapsed on itself seeing that it has been integrated in the scar tissue. Moreover the composition of the new wall, i.e. of the tissue of the scar, has shown to be mainly mature granulation tissue not covered by urothelium.

Therefore the device in PGA textile reinforced with strips in PGA textile has demonstrated that it has an insufficient mechanical consistency during the time of regeneration of the cells of the bladder, influencing the growth of the new biological wall tissue of the portion of bladder removed and the growth of the urothelium: this has meant that the growing tissue did not go to replace that being absorbed, growing therefore in other directions. The result is a bladder which tends to have an asymmetrical and abnormal shape, different from the original one, therefore potentially irritating for the other surrounding organs.

This is probably also due to the fact that the domed device in PGA textile with reinforcements in PGA textile shows a decrease in rigidity during the time of growth of the neotissue.

On the contrary the present heat-formed frame made in PGA/PLA has shown, despite its absorbability, a constant rigidity during the time of growth of the bladder neotissue.

Numerous detail modifications and changes, within the reach of a person skilled in the art, may be made to the present embodiments of the invention, in any case coming within the scope of the invention disclosed by the annexed claims.

The invention claimed is:

1. An enlargement prosthesis of an atrophied bladder in the form of a self-supporting domed cap with a round profile, said cap being formed by:
    an absorbable textile that is texturized and made with multifilament or monofilament yarns deriving from polyglycolide or polyglycolic acid (PGA) fibers, said absorbable textile being supported by a non-porous hot molded self-supporting frame with a domed profile and which is flexible and harmonic, the frame being rigid and formed by a plurality of curved and heat-formed reinforcement strips made with an absorbable copolymer in poly(lactic-co-glycolic)acid (PGA/PLA), each of said strips forming a portion of an arc which extends from the top of the frame downwards and being substantially rigid but elastic and with a slight curvature which allows the frame to have a domed configuration, the textile having a circular plan profile.

2. The enlargement prosthesis according to claim 1, wherein said frame is attached to the textile by absorbable sutures.

3. The enlargement prosthesis according to claim 1, wherein the thickness of the textile ranges from 0.1 mm to 2 cm.

4. The enlargement prosthesis according to claim 1, wherein the yarns of the textile have a dimension comprised between 50 and 200 deniers.

5. The enlargement prosthesis according to claim 1, wherein the yarns of the textile are 75 deniers/30 filaments.

6. The enlargement prosthesis according to claim 1, wherein the textile is a warp-knitted textile.

7. The enlargement prosthesis according to claim 1, wherein the textile is a texturized textile.

8. The enlargement prosthesis according to claim 1, wherein the reinforcement strips which form the domed frame have a thickness comprised between 0.1 and 10 mm.

9. The enlargement prosthesis according to claim 1 wherein the PGA/PLA copolymer of the frame is made of 30% PGA and of 70% PLA.

10. The enlargement prosthesis according to claim 1 wherein the PLA/PGA copolymer is a poly(L-lactic-co-glycolic) copolymer (PLLA/PGA), the L-lactic acid being 82-88% in moles, the glycolic acid being 18-12% in moles.

11. The enlargement prosthesis according to claim 1, wherein relative suturing of the cap to the bladder is performed with suture threads made of absorbable PGA material.

12. The enlargement prosthesis cap according to claim 2, wherein the thickness of the textile ranges from 0.3 to 0.6 mm.

13. The enlargement prosthesis cap according to claim 2, wherein the thickness of the textile ranges from 0.4 to 0.53 mm.

14. The enlargement prosthesis cap according to claim 2, wherein the reinforcement strips which form the domed frame have a thickness comprised between 0.5 and 2 mm.

15. The enlargement prosthesis cap according to claim 2, wherein the absorbable sutures include at least one monofilament in polydioxanone (PDO) with slow absorption.

16. The enlargement prosthesis according to claim 3, wherein the thickness of the textile ranges from 0.3-0.6 mm.

17. The enlargement prosthesis according to claim 16, wherein the thickness of the textile ranges from 0.4-0.53 mm.

18. The enlargement prosthesis according to claim 17, wherein the thickness of the textile ranges from 0.4-0.53 mm, including 0.45 mm.

19. The enlargement prosthesis according to claim 8, wherein the reinforcement strips which form the domed frame have a thickness comprised between 0.5 and 2 mm, including about 1 mm.

20. The enlargement prosthesis according to claim 1, wherein the domed configuration is defined by portions of the frame extending from the top of the frame downward and a volume defined between the downwardly-extending portions of the frame, the volume being about 200 cc.

* * * * *